United States Patent [19]
Suzuki et al.

[11] Patent Number: 5,919,346
[45] Date of Patent: Jul. 6, 1999

[54] OXYGEN CONCENTRATION-DETECTING DEVICE FOR INTERNAL COMBUSTION ENGINES

[76] Inventors: Norio Suzuki, c/o Honda R&D Co., Ltd., of No. 4-1, Chuo 1-chome, Wako-shi, Saitama; Daisuke Shimizu; Yukio Noda, both of c/o Honda R&D Co., Ltd., of No. 4-1, Chuo 1-chome, Wako-shi, Saitama-ken, all of Japan

[21] Appl. No.: 08/940,945

[22] Filed: Sep. 30, 1997

[30] Foreign Application Priority Data

Oct. 3, 1996 [JP] Japan .................................. 8-281319

[51] Int. Cl.⁶ .................................................. G01N 27/407
[52] U.S. Cl. ........................ 204/424; 204/425; 204/428; 205/784.5; 205/785
[58] Field of Search .................... 204/421–429; 205/783.5, 784, 784.5, 785

[56] References Cited

U.S. PATENT DOCUMENTS

| | | | |
|---|---|---|---|
| 4,715,343 | 12/1987 | Kinoshita | 204/425 |
| 4,860,712 | 8/1989 | Nakajima et al. | 204/425 |
| 4,915,082 | 4/1990 | Uchinami et al. | 204/425 |

*Primary Examiner*—T. Tung
*Attorney, Agent, or Firm*—Nikaido Marmelstein Murray & Oram, LLP

[57] ABSTRACT

An oxygen concentration-detecting device for an internal combustion engine includes an oxygen concentration sensor arranged in the exhaust system of the engine, for detecting concentration of oxygen present in exhaust gases emitted from the engine. Energization of a heater for heating the oxygen concentration sensor is started when the ignition switch is turned on. The energization of the heater is stopped after a predetermined time period has elapsed after the turning-on of the ignition switch.

2 Claims, 4 Drawing Sheets

OXYGEN CONCENTRATION-DETECTING DEVICE FOR INTERNAL COMBUSTION ENGINES

BACKGROUND OF THE INVENTION

1. Field of the Invention

This invention relates to an oxygen concentration-detecting device for internal combustion engines, which detects the concentration of oxygen present in exhaust gases emitted from an internal combustion engine by using an oxygen concentration sensor arranged in the exhaust system of the engine.

2. Prior Art

Conventionally, a temperature control device for controlling the temperature of an oxygen concentration sensor arranged in the exhaust system of an internal combustion engine has been proposed e.g. by Japanese Laid-Open Patent Publication (Kokai) No. 60-235047, which accelerates heating of the oxygen sensor immediately after an ignition switch of the engine is turned on or a starter switch of the same is detected to be turned off, by maximizing electric power supplied to a heater of the oxygen sensor, thereby quickly activating the oxygen concentration sensor so as to start the air-fuel ratio feedback control at an early stage for improved exhaust emission characteristics of the engine.

The proposed temperature control device, however, suffers from the problem that when the heater is energized by supplying the maximum power thereto after the ignition switch is turned on, if the engine is not started with the ignition switch remaining on, the electric power stored in a battery of the engine continues to be consumed by the heater without generation of electric power by an alternator, resulting in a drop in the output voltage of the battery.

Further, when the engine is started under a low temperature condition, if the battery voltage is low, it can be difficult to start the engine by supplying the maximum electric power to the heater.

SUMMARY OF THE INVENTION

It is a first object of the invention to provide an oxygen concentration-detecting device for an internal combustion engine, which is capable of preventing the electric power stored in the battery of the engine from continuing to be consumed by a heater of an oxygen concentration sensor arranged in the exhaust system of the engine, even if the engine fails to be started with an ignition switch of the engine left on.

It is a second object of the invention to provide an oxygen concentration-detecting device for an internal combustion engine, which is capable of enabling the engine to smoothly start even if the battery voltage is low when the engine is started under a low temperature condition.

To attain the first object, according to a first aspect of the invention, there is provided an oxygen concentration-detecting device for an internal combustion engine having an exhaust system, and an ignition switch, the oxygen concentration-detecting device including an oxygen concentration sensor arranged in the exhaust system, for detecting concentration of oxygen present in exhaust gases emitted from the engine, heating means for heating the oxygen concentration sensor, and energization-starting means responsive to turning-on of the ignition switch, for starting energization of the heating means.

The oxygen concentration-detecting device according to the first aspect of the invention is characterized by comprising stopping means for stopping the energization of the heating means after a predetermined time period has elapsed after the turning-on of the ignition switch.

Preferably, the oxygen concentration-detecting device includes engine start-detecting means for detecting whether or not the engine has been started after the turning-on of the ignition switch, and the stopping means stops the energization of the heating means when the engine is not started before the predetermined time period elapses.

To attain the second object, according to a second aspect of the invention, there is provided an oxygen concentration-detecting device for an internal combustion engine having an exhaust system, and an ignition switch, the oxygen concentration-detecting device including an oxygen concentration sensor arranged in the exhaust system, for detecting concentration of oxygen present in exhaust gases emitted from the engine, heating means for heating the oxygen concentration sensor, energization-starting means responsive to turning-on of the ignition switch, for starting energization of the heating means, and temperature-detecting means for detecting a temperature of the engine.

The oxygen concentration-detecting device according to the second aspect of the invention is characterized by comprising:

determining means for determining whether or not the temperature of the engine detected by the temperature-detecting means is below a predetermined value; and inhibiting means for inhibiting the energization of the heating means when the temperature of the engine detected by the temperature-detecting means is below the predetermined value.

Preferably, the engine includes a battery for supplying electric power to the heating means to energize the heating means, the oxygen concentration-detecting device including voltage-detecting means for detecting output voltage of the battery, the inhibiting means inhibiting the energization of the heating means when the temperature of the engine detected by the temperature-detecting means is below the predetermined value and at the same time the output voltage of the battery detected by the voltage-detecting means is below a predetermine value.

The above and other objects, features, and advantages of the invention will be become more apparent from the following detailed description taken in conjunction with the accompanying drawings.

DETAILED DESCRIPTION

The invention will now be described in detail with reference to the drawings showing an embodiment thereof.

Figure 1:
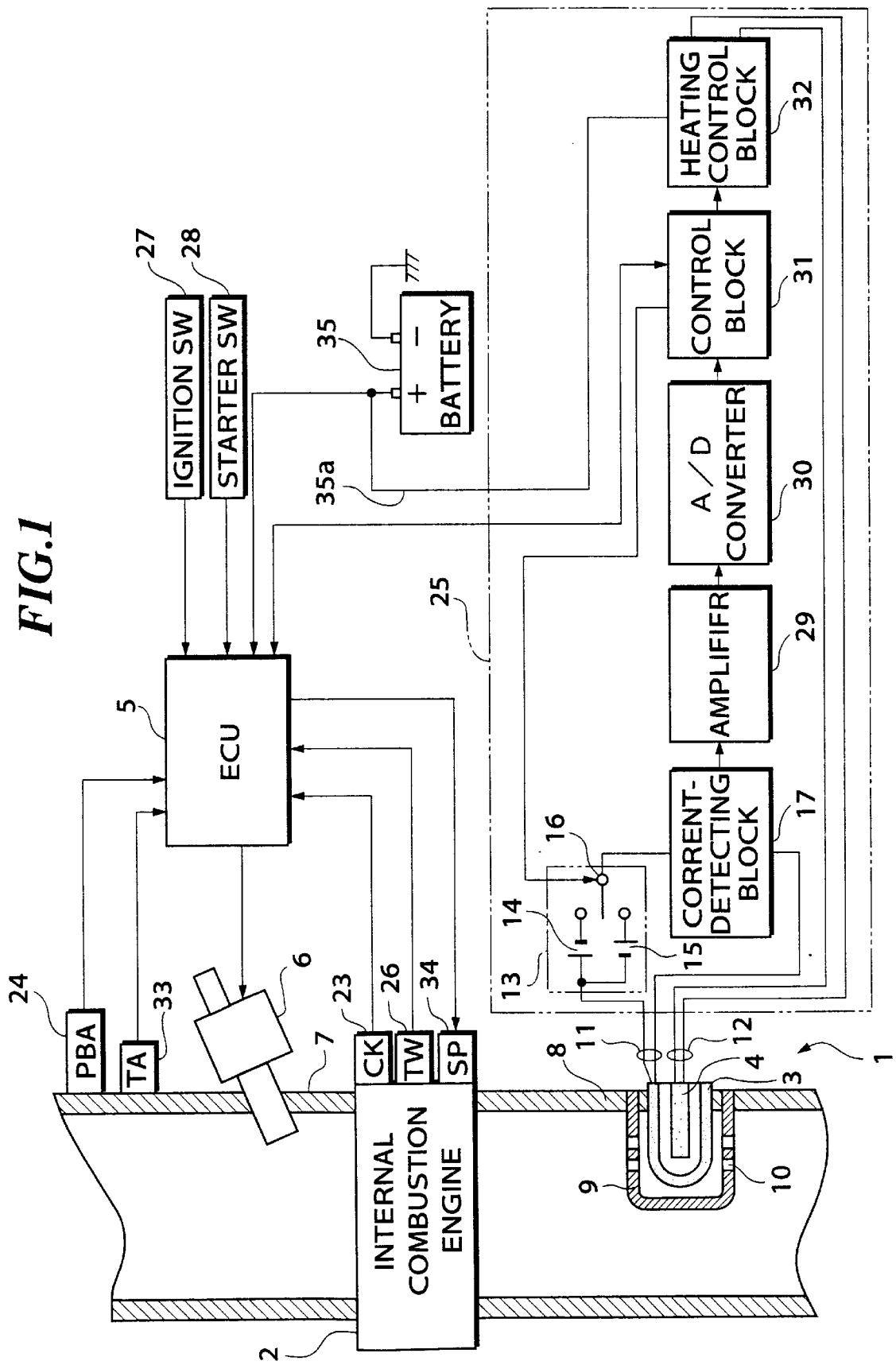
FIG. 1 is a block diagram showing the whole arrangement of an oxygen concentration-detecting device according to an embodiment of the invention, and a control system for an internal combustion engine, which incorporates the oxygen concentration-detecting device.

Referring first to FIG. 1, there is shown the whole arrangement of an oxygen concentration-detecting device according to an embodiment of the invention, and a control system for an internal combustion engine (hereinafter referred to as "the engine") to which is applied the oxygen concentration-detecting device.

In the figure, reference numeral 2 designates an internal combustion engine e.g. of a four-cylinder type. Connected to the cylinder block of the engine 2 is an intake pipe 2 into which are inserted fuel injection valves 6 and an intake an intake pipe absolute pressure (PBA) sensor 24. The fuel injection valve 6 is connected to a fuel pump, not shown, and at the same time electrically connected to an electronic control unit (ECU) 5, to have injection timing and fuel injection periods (valve opening periods) thereof controlled by signals from the ECU 5.

The intake pipe absolute pressure (PBA) sensor 24 supplies an electric signal indicative of the sensed intake pipe absolute pressure PBA to the ECU 5. An intake air temperature sensor (TA) 33 is inserted into the intake pipe at a location downstream of the intake pipe absolute pressure (PBA) sensor 24 for supplying an electric signal indicative of the sensed intake air temperature TA to the ECU 5.

The engine 2 has spark plugs (SP) 34 provided for respective cylinders and electrically connected to the ECU 5 to have ignition timing thereof controlled by signals therefrom.

An engine coolant temperature (TW) sensor 26, which is formed of a thermistor or the like, is mounted in the cylinder block of the engine 2, for supplying an electric signal indicative of the sensed engine coolant temperature TW to the ECU 5.

Also electrically connected to the ECU 5 are an ignition switch 27 and a starter switch 2, which are turned on to thereby start an ignition system and a starter motor, respectively. Further, a power supply line 35a for a storage battery 35 is connected to the ECU 5 via which the ECU 5 detects battery voltage VB.

Arranged in facing relation to a camshaft or a crankshaft of the engine 2, neither of which is shown, is a crank angle (CK) sensor 23 which is comprised of an engine rotational speed (NE) sensor, a cylinder-discriminating (CYL) sensor, and a crank angle position (CRK) sensor. The engine rotational speed (NE) sensor generates a pulse (TDC signal pulse) at a predetermined crank angle position of each cylinder corresponding to the start of the intake stroke of the cylinder whenever the crankshaft of the engine 2 rotates through 180 degrees if the engine is a four-cylinder type. The cylinder-discriminating sensor generates a pulse (CYL signal pulse) at a predetermined crank angle position of a particular cylinder a predetermined angle before a TDC position corresponding to the start of the intake stroke of the cylinder. The crank angle position (CRK) sensor generates a pulse (CRK signal pulse) at each of predetermined crank angle positions whenever the crankshaft rotates through a predetermined angle (e.g. 30 degrees) smaller than the rotational angle interval of generation of the TDC signal pulse. These signal pulses are supplied to the ECU 5 to be used for timing control in carrying out operations of the control system for determining a fuel injection amount (fuel injection period), fuel injection timing, ignition timing, etc., as well as for detecting the engine rotational speed NE.

A three-way catalyst, not shown, as an exhaust gas-purifying device is arranged within an exhaust pipe 8 connected to the cylinder block of the engine 2, for purifying noxious components such as HC, CO, and NOx.

The ECU 5 is comprised of an input circuit having the functions of shaping the waveforms of input signals from various sensors, shifting the voltage levels of sensor output signals to a predetermined level, converting analog signals from analog-output sensors to digital signals, and so forth, a central processing unit ("the CPU"), a memory device comprised of a ROM storing various operational programs which are executed by the CPU and various maps, referred to hereinafter, and a RAM for storing results of calculations from the CPU, etc., and an output circuit which outputs driving signals to the fuel injection valves 6, etc.

The CPU operates in response to signals from various sensors including the above mentioned ones to determine various operating conditions in which the engine 2 is operating, including an air-fuel ratio feedback region, and calculates, based upon the determined operating conditions, the valve opening period or fuel injection period Tout over which the fuel injection valves 6 are to be opened, by the use of the following equation (1):

$$Tout = To \times K1 + K2 \qquad (1)$$

where To represents a basic fuel amount, or more specifically, a basic fuel injection period, which is determined in accordance with the engine rotational speed NE and the intake pipe absolute pressure PBA. K1, K2 represent correction coefficients or correction variables which are set according to engine operating parameters to such values as optimize engine operating characteristics, such as fuel consumption and engine accelerability.

On the other hand, the oxygen concentration-detecting device 1 is comprised of a LAF sensor 3, a main unit 25, and so forth. The LAF sensor 3 is inserted into the exhaust pipe 8 of the engine 2, which has an output signal line thereof detachably connected to the main unit 25 by a connector, not shown. The LAF sensor 3 is comprised of a solid electrolyte element in the form of a cup, and so forth, with a heater 4 mounted therein. The heater 4 has a sufficient heating capacity for activating the LAF sensor 3. Further, the LAF sensor 3 is enclosed within a cover 9 formed with small through holes 10 for permitting exhaust gases to flow into the cover 9, whereby the LAF sensor 3 is protected from being directly exposed to exhaust gases flowing in the exhaust pipe 8, with enhanced heat insulation of the LAF sensor 3.

On the other hand, the main unit 25 is provided with a bias control block 13, a current-detecting block 17, an amplifier 29, an A/D converter 30, a control block 31 and a heating control block 32. One of lead wires 11 connected to the LAF sensor 3 is connected to the bias control block 13, whereas the other of the lead wires 11 is connected to the current-detecting block 17. Two lead wires 12 connected to the heater 4 and a power supply line 35a connected to the storage battery 35 are connected to the heating control block 32. The heating control block 32 supplies the heater 4 with power from the battery 35 according to an energizing control process, described hereinafter, carried out by the control block 31.

The control block 31, which is electrically connected to the ECU 5, refers to a flag set or reset according to a start-time temperature control process, described hereinafter, carried out by the ECU 5, and delivers a signal indicative of the oxygen concentration (air-fuel ratio A/F)

detected by the LAF sensor 3 to the ECU 5 in response to a readout request from the ECU 5.

The bias control block 13 has a positive bias source 14, a negative bias source 15, and a selector switch 16. The selector switch 16 changes over the polarity of the bias voltage to be applied to the LAF sensor 3, in response to a signal from the control block 31.

The current-detecting block 17 supplies a signal indicative of electric current supplied from the LAF sensor 3 to the amplifier 29 where the signal is amplified and shaped, and the resulting signal is delivered to the A/D converter 30.

Figure 2:
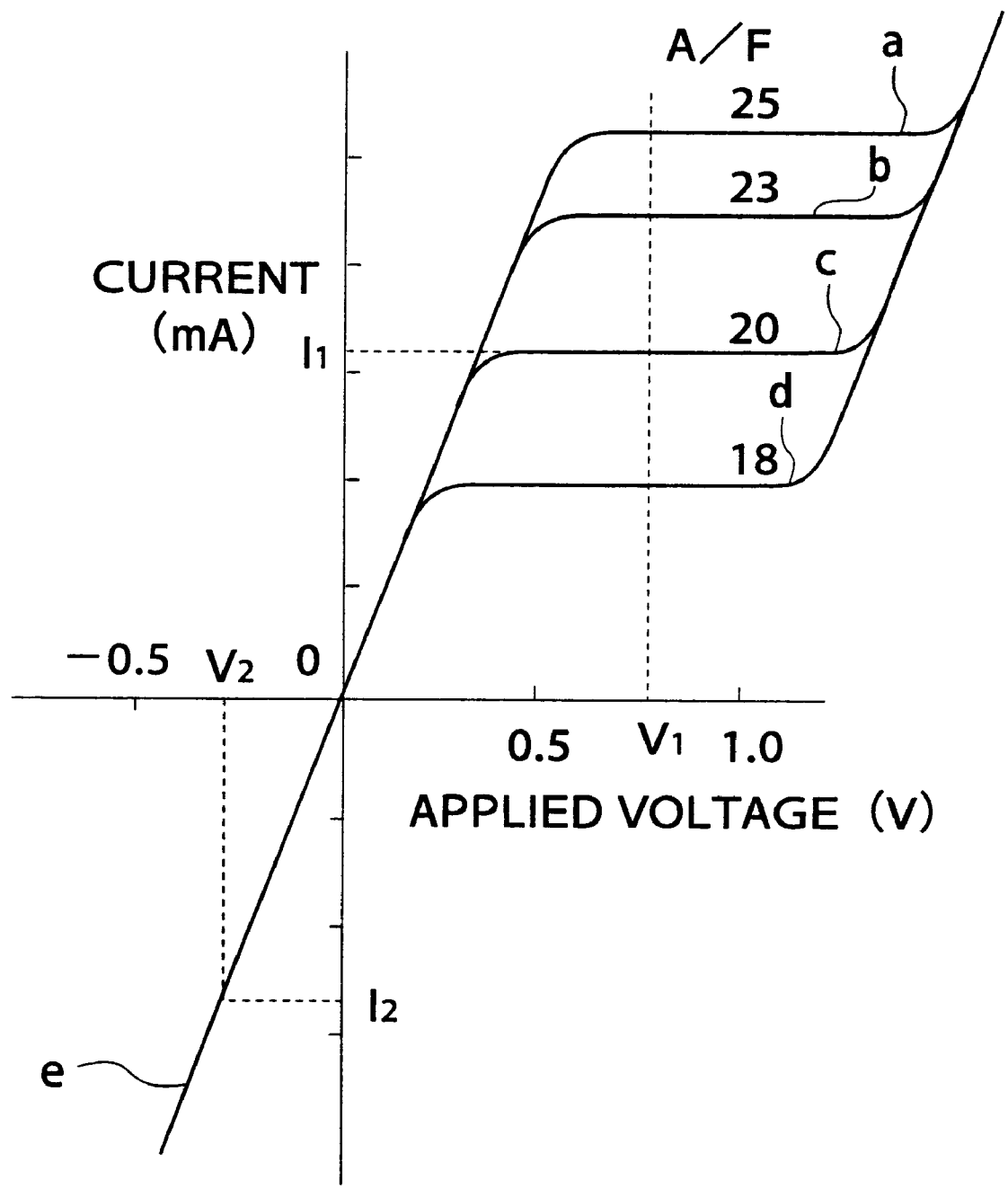
FIG. 2 is a diagram showing an output characteristic of a LAF sensor 3 appearing in FIG. 1.

FIG. 2 shows an output characteristic of the LAF sensor 3. If the LAF sensor 3 is active, when the positive bias voltage is applied to the LAF sensor 3, critical current values (a, b, c, and d shown in the figure) are proportional to partial pressure of oxygen and hence the concentration of oxygen present in exhaust gases, that is, the air-fuel ratio (A/F) can be linearly detected by reading out the critical current values. On the other hand, to maintain the LAF sensor 3 active, it is required to hold the temperature of the LAF sensor 3 within a predetermined high temperature range, e.g. at a temperature of approximately 650° C. The temperature of the LAF sensor 3 cannot be held within the predetermined high temperature range by the heat of the exhaust gases from the engine 2 alone, and hence it is required to apply the bias voltage to the LAF sensor 3, and measure the internal resistance (gradient e shown in the figure) of the LAF sensor based on the detected value of electric current flowing therethrough, thereby heating the LAF sensor 3 with the heater 4 such that the internal resistance of the LAF sensor 3 is constant.

The process of applying the bias voltage to the LAF sensor 3 to detect the value of electric current flowing therethrough so as to maintain the LAF sensor 3 in an active state is similar to the process of detecting the oxygen concentration. Therefore, the oxygen concentration-detecting device 1 carries out the process of maintaining the LAF sensor 3 in an active state and the process of detecting the oxygen concentration, alternately at predetermined time intervals.

In the oxygen concentration-detecting process, the selector switch 16 is connected to the positive bias source 14 in response to a control signal from the control block 31, to thereby apply the positive bias voltage V1 to the LAF sensor 3 (see FIG. 2). Then, the current value I1 supplied from the LAF sensor 3 is detected by the current-detecting block 17. The signal indicative of the detected current value is amplified and has its waveform shaped by the amplifier 29, and then converted into a digital value by the A/D converter 30. The control block 31 calculates the concentration of oxygen present in exhaust gases (air-fuel ratio) based on the digitized value and temporarily stores the calculated oxygen concentration value in a memory within the control block 31. The oxygen concentration value temporarily stored in the memory is read out upon request from the ECU 5, and used for the air-fuel ratio feedback control.

In the process of maintaining the LAF sensor 3 in an active state, the selector switch 16 is connected to the negative bias source 15 in response to a control signal from the control block 31, to thereby apply the negative bias voltage V2 to the LAF sensor 3 (see FIG. 2). Then, the current value I2 supplied from the LAF sensor 3 is detected by the current-detecting block 17. The signal indicative of the detected current value is amplified and has its waveform shaped by the amplifier 29, and then converted into a digital value by the A/D converter 30. The control block 31 measures the internal resistance of the LAF sensor 3 based on the digitized value to output a control signal to the heating control block 32 such that the measured internal resistance is always held constant. The heating control block 32 connects or disconnects the power supply line 35a connected to the battery 35 to or from the lead wires 12 connected to the heater 4 in response to the control signal to thereby heat the LAF sensor 3.

Figure 3:
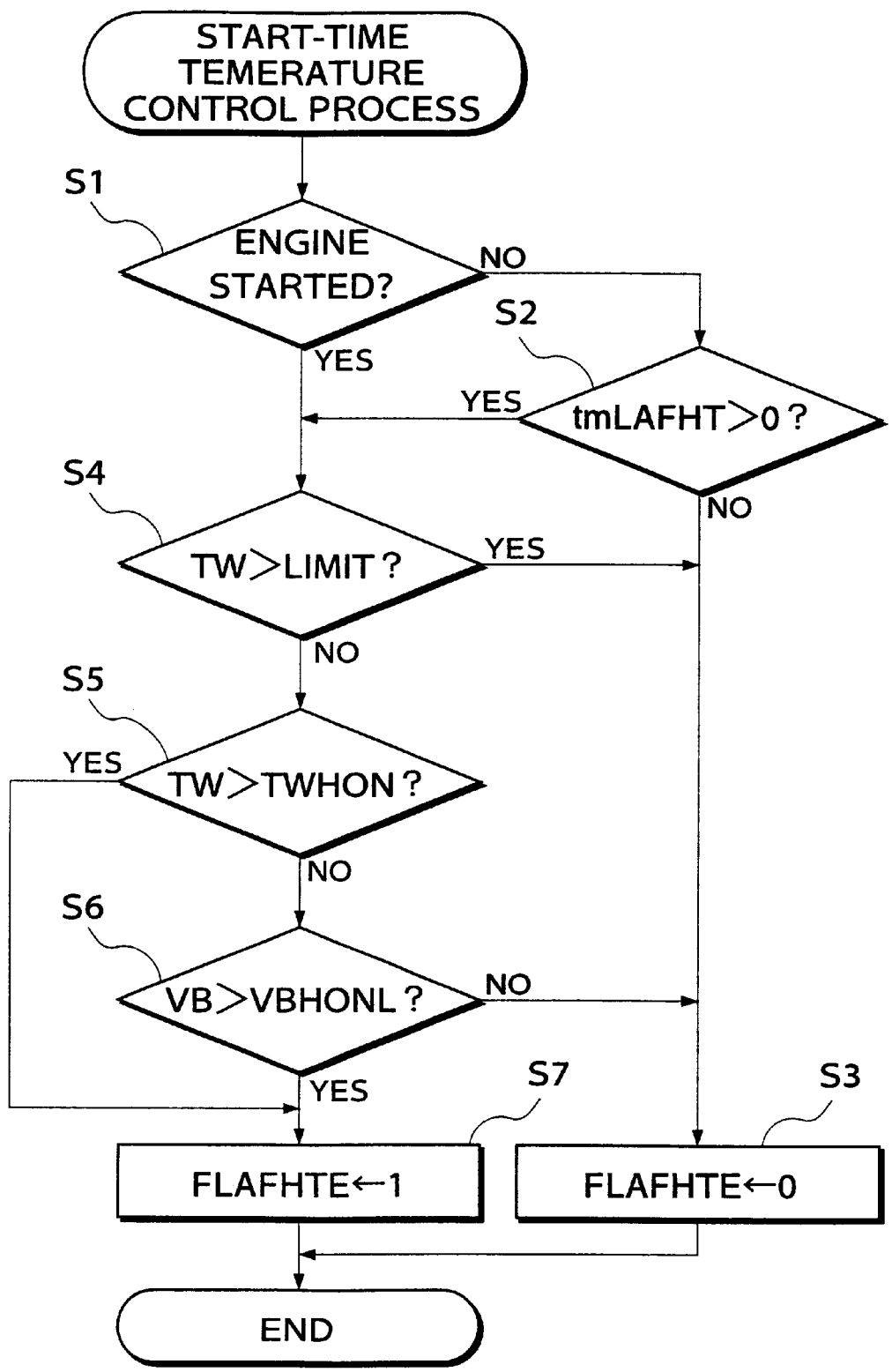
FIG. 3 is a flowchart showing a routine for carrying out a start-time temperature control process for controlling the temperature of the LAF sensor, which is started to be executed by an ECU 5 appearing in FIG. 1 in synchronism with turning-on of an ignition switch 27 appearing in the same, and thereafter executed at predetermined time intervals (10 msec)

Next, the start-time temperature control process executed by the ECU 5 will be described. FIG. 3 shows a routine for carrying out the start-time temperature control process of the LAF sensor, which is started to be executed by the ECU 5 in synchronism with turning-on of the ignition switch 27 and thereafter executed at predetermined time intervals (10 msec).

Referring to FIG. 3, first, the ECU 5 determines at a step S1 whether or not the engine 2 is being cranked. This determination may be carried out based on whether the starter switch 28 is ON, or whether the engine rotational speed NE detected by the crank angle sensor 23 is within a predetermined rotational speed range (60 to 100 rpm).

If it is determined at the step S1 that the engine 2 is not in operation, it is determined at a step S2 whether or not the count of a downtimer tmLAFHT is larger than "0". In the present embodiment, the downtimer tmLAFHT is set to an initial value of "10 seconds" to start measuring time elapsed, upon turning-on of the ignition switch 27. When the engine 2 remains inoperative even after 10 seconds have passed after the ignition switch 27 is turned on, a flag FLAFHTE indicative of permission of energizing the heater 4 is reset to "0" to thereby inhibit energization of the same at a step S3, followed by terminating the program. The value of the flag FLAFHTE is referred to by the control block 31 according to the energizing control process, described hereinafter, at predetermined time intervals.

On the other hand, when it is determined at the step S1 before 10 seconds have passed after turning-on of the ignition switch 27 that the engine 2 has been started, a signal from the engine coolant temperature (TW) sensor 26 is read in to detect the engine coolant temperature TW, and then it is determined at a step S4 whether or not the detected engine coolant temperature TW exceeds a limit value. If the engine coolant temperature TW exceeds the limit value, i.e. if the TW sensor 26 is faulty, the flag FLAFHTE indicative of the permission of energizing the heater 4 is reset to "0" to thereby inhibit energization of the same, followed by terminating the program.

If the engine coolant temperature TW does not exceed the limit value at the step S4, it is determined at a step S5 whether or not the engine coolant temperature TW is higher than a predetermined temperature value TWHON. In the present embodiment, the predetermined temperature value TWHON is set to "−10° C.". If the engine coolant temperature TW is higher than the predetermined temperature value TWHON, the flag FLAFHTE indicative of the permission of energizing the heater 4 is set to "1" to thereby permit energization of the same at a step S7, followed by terminating the program.

If the engine coolant temperature TW is equal to or lower than the predetermined temperature value TWHON at the step S5, it is determined at a step S6 whether or not the battery voltage VB is higher than a predetermined voltage value VBHONL. In the present embodiment, the predetermined voltage value VBHONL is set to 10 volts. If the battery voltage VB is higher than the predetermined voltage value VBHONL, the flag FLAFHTE indicative of the permission of energization of the heater 4 is set to "1" to thereby permit energization of the same, followed by terminating the program.

On the other hand, if it is determined at the step S6 that the battery voltage VB is equal to or lower than the predetermined voltage value VBHONL, the flag FLAFHTE indicative of the permission of energization of the heater 4 is reset to "0" to thereby inhibit energization of the same, followed by terminating the program.

Figure 4:
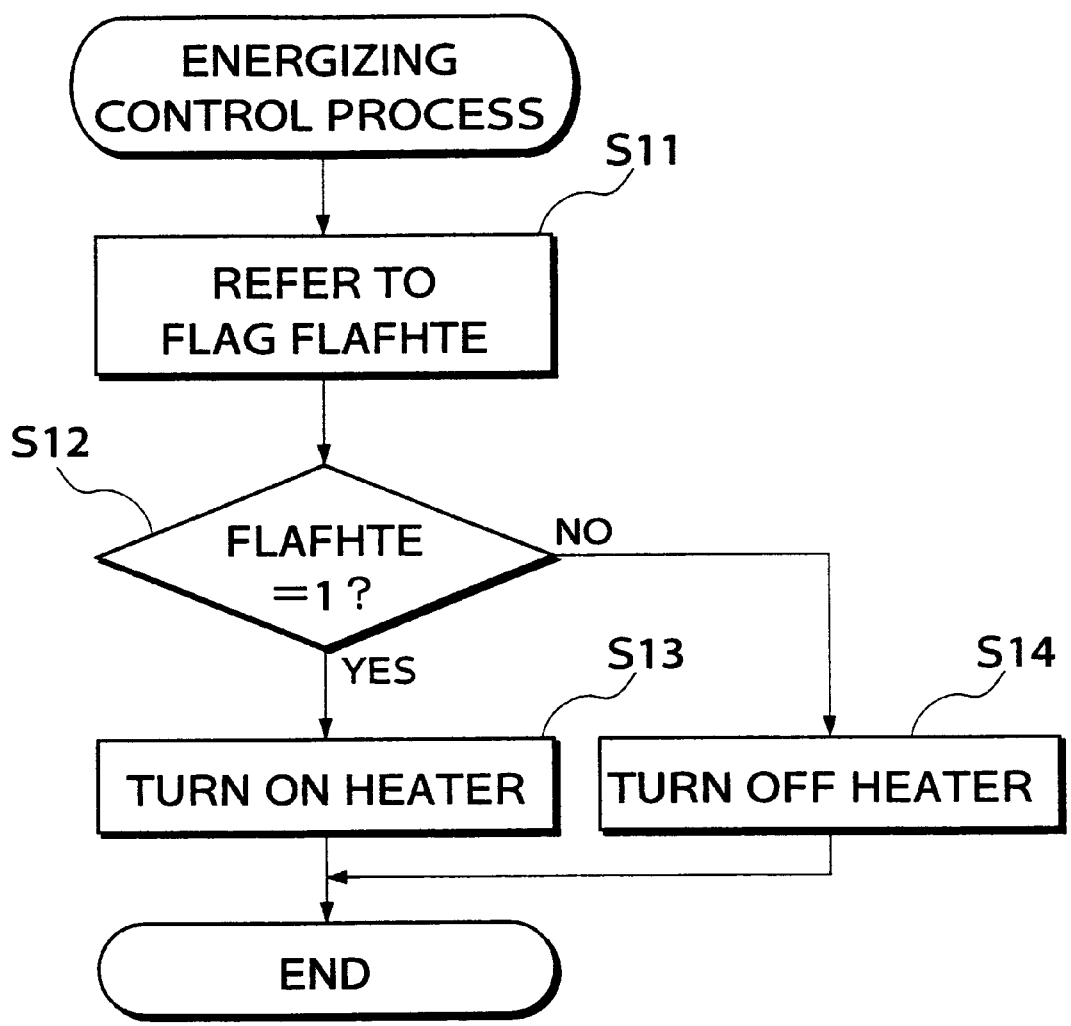
FIG. 4 is a flowchart showing a routine for carrying out an energizing control process executed by a control block 31 appearing FIG. 1.

FIG. 4 shows a routine for carrying out the energizing control process, which is executed by the control block 31. This process is executed by interrupt handling requested at predetermined time intervals. When the process is started, first, at a step S11, the control block 31 refers to the flag FLAFHTE stored in the memory within the ECU 5.

Then, it is determined at a step S12 whether or not the flag FLAFHTE is set to "1". If the flag FLAFHTE assumes "1", a control signal is delivered to the heating control block 32 to thereby start the control of energization of the heater 4 at a step S13. The heating control block 32 connects or disconnects the power supply line 35a connected to the battery 35 to or from the lead wires 12 connected to the heater 4 in response to the control signal, to thereby heat the LAF sensor 3 such that the temperature of the LAF sensor is held within the predetermined high temperature range.

On the other hand, if the flag FLAFHTE is reset to "0", the control signal is not output to the heating control block and the control of energization of the heater 4 is stopped at a step S14.

As described above, according to the present embodiment, after turning-on of the ignition switch 27, energization of the heater 4 for heating the LAF sensor 3 is permitted. However, if the engine 2 is not started even after a predetermined time period has elapsed, the energization of the heater 4 is stopped. This makes it possible to prevent the power of the battery 35 from continuing to be consumed by the heater 4 without generation of electric power by the alternator, even if the ignition switch 27 is left ON without the engine 2 being started.

Further, even if the engine 2 is started within the predetermined time period, when the engine coolant temperature TW and the battery voltage VB are concurrently low, the energization of the heater 4 is inhibited, whereby it is possible to avoid poor startability of the engine.

It should be noted that, although in the present embodiment, the start-time temperature control is carried out by the ECU 5 to thereby set or reset the flag FLAFHTE indicative of permission of energization of the heater 4, this is not limitative, but this control may be executed by the control block 31 instead of the ECU 5. In such a case, signal lines to the ignition switch 27, the starter switch 28 and so forth are connected to the control block 31, which makes it possible to decrease the processing load or burden on the ECU 5.

Further, although in the present embodiment, the LAF sensor is employed as an oxygen concentration sensor, it goes without saying that the present invention can be applied to an oxygen concentration sensor (O2 sensor) which has an output characteristic that the output drastically changes between a rich value and a lean value with respect to a stoichiometric air-fuel ratio as the air-fuel ratio of exhaust gases changes across the stoichiometric air-fuel ratio and used for determining whether a mixture supplied to the engine is rich or lean, during air-fuel ratio feedback control.

What is claimed is:

1. In an oxygen concentration-detecting device for an internal combustion engine having an exhaust system, and an ignition switch, said oxygen concentration-detecting device including an oxygen concentration sensor arranged in said exhaust system, for detecting concentration of oxygen present in exhaust gases emitted from said engine, heating means for heating said oxygen concentration sensor, energization-starting means responsive to turning-on of said ignition switch, for starting energization of said heating means, and temperature-detecting means for detecting a temperature of said engine, the improvement comprising:
 determining means for determining whether or not said temperature of said engine detected by said temperature-detecting means is below a predetermined value; and
 inhibiting means for inhibiting said energization of said heating means when said temperature of said engine detected by said temperature-detecting means is below said predetermined value.

2. An oxygen concentration-detecting device according to claim 1, wherein said engine includes a battery for supplying electric power to said heating means to energize said heating means, said oxygen concentration-detecting device including voltage-detecting means for detecting output voltage of said battery,
 said inhibiting means inhibiting said energization of said heating means when said temperature of said engine detected by said temperature-detecting means is below said predetermined value and at the same time said output voltage of said battery detected by said voltage-detecting means is below a predetermine value.

\* \* \* \* \*